United States Patent
Lee et al.

(10) Patent No.: US 9,492,526 B2
(45) Date of Patent: Nov. 15, 2016

(54) POLYNUCLEOTIDES FOR TREATING ONCOGENIC VIRAL POLYPEPTIDE POSITIVE TUMORS

(71) Applicant: SANFORD HEALTH, Sioux Falls, SD (US)

(72) Inventors: John H. Lee, Sioux Falls, SD (US); Daniel W. Vermeer, Sioux Falls, SD (US)

(73) Assignee: Sanford Health, Sioux Falls, SD (US)

( * ) Notice: Subject to any disclaimer, the term of this patent is extended or adjusted under 35 U.S.C. 154(b) by 0 days.

(21) Appl. No.: 14/373,844

(22) PCT Filed: Jan. 23, 2013

(86) PCT No.: PCT/US2013/022696
§ 371 (c)(1),
(2) Date: Jul. 22, 2014

(87) PCT Pub. No.: WO2013/112549
PCT Pub. Date: Aug. 1, 2013

(65) Prior Publication Data
US 2015/0023996 A1   Jan. 22, 2015

Related U.S. Application Data

(60) Provisional application No. 61/590,089, filed on Jan. 24, 2012.

(51) Int. Cl.
*A61K 39/12* (2006.01)
*C07K 14/005* (2006.01)
*C12N 7/00* (2006.01)
*A61K 39/00* (2006.01)

(52) U.S. Cl.
CPC .......... *A61K 39/12* (2013.01); *A61K 39/0011* (2013.01); *C07K 14/005* (2013.01); *C12N 7/00* (2013.01); *A61K 2039/5256* (2013.01); *A61K 2039/5258* (2013.01); *A61K 2039/53* (2013.01); *A61K 2039/543* (2013.01); *A61K 2039/585* (2013.01); *C12N 2710/10042* (2013.01); *C12N 2710/10343* (2013.01); *C12N 2710/20022* (2013.01); *C12N 2710/20032* (2013.01); *C12N 2710/20034* (2013.01); *C12N 2710/20071* (2013.01)

(58) Field of Classification Search
None
See application file for complete search history.

(56) References Cited

U.S. PATENT DOCUMENTS

| 6,342,224 B1 | 1/2002 | Bruck et al. |
| 2007/0275003 A1 | 11/2007 | Cassetti et al. |
| 2010/0303838 A1 | 12/2010 | Silvestre et al. |

FOREIGN PATENT DOCUMENTS

| WO | 9910375 A2 | 3/1999 |
| WO | 99/61608 A2 | 12/1999 |
| WO | 2008138648 A1 | 11/2008 |
| WO | 2010/129339 | 11/2010 |

OTHER PUBLICATIONS

Antinore et al. The human papillomavirus type 16 E7 gene product interacts with and trans-activates the AP1 family of transcription factors. EMBO J. Apr. 15, 1996;15(8):1950-60.*
NP_041325.1. transforming protein [Human papillomavirus type 16] Oct. 27, 2010.*
Nakagawa et al. Mutational Analysis of Human Papillomavirus Type 16 E6 Protein: Transforming Function for Human Cells and Degradation of p53 in Vitro. Virology 212, 535-542 (1995).*
Munger et al. Mechanisms of Human Papillomavirus-Induced Oncogenesis. J. Virol. 2004, 78: 11451-11460.*
Helt et al. Destabilization of the Retinoblastoma Tumor Suppressor by Human Papillomavirus Type 16 E7 is Not Sufficient to Overcome Cell Cycle Arrest in Human Keratinocytes. J. Virol. 2001, 75:6737-6747.*
Nguyen et al. Human Papillomavirus Type 16 E7 Maintains Elevated Levels of the cdc25A Tyrosine Phosphatase during Deregulation of Cell Cycle Arrest. J. Virol. 2002. 76:619-632.*
Nguyen et al. The PDZ Ligand Domain of the Human Papillomavirus Type 16 E6 Protein is Required for E6's Induction of Epithelial Hyperplasia In Vivo. J. Virol. 2003. 77: 6957-6964.*
International Search Report for PCT/US2013/022696, mailed May 8, 2013.
Chema et al., "Multiple sequence alignment with the Clustal series of programs," Nucleic Acids Res., 31(13):3497-500 (2003).

(Continued)

*Primary Examiner* — Nick Zou
(74) *Attorney, Agent, or Firm* — McDonnell Boehnen Hulbert & Berghoff LLP

(57) ABSTRACT

This document relates to polynucleotides encoding antigenic polypeptides to induce an immune response to oncogenic viral polypeptides. Also provided are compositions comprising polynucleotides encoding antigenic polypeptides, and methods of use. In the provided methods, the virus can be a human papilloma virus. In some embodiments, a method for killing a cell expressing a first oncogenic viral polypeptide in a subject is provided. The method includes administering to the subject a composition in an amount sufficient to initiate an immune response against the first oncogenic viral peptide, where the composition comprises a pharmaceutically acceptable carrier and a polynucleotide provided herein and the immune response is effective to cause a cytotoxic effect in the cell. In some embodiments, the polynucleotide includes a second nucleotide sequence encoding a second antigenic polypeptide. The first oncogenic viral polypeptide can be E6 and the second oncogenic viral polypeptide can be E7.

15 Claims, 12 Drawing Sheets

(56) References Cited

OTHER PUBLICATIONS

Amalfitano et al. (1998), "Production and Characterization of Improved Adenovirus Vectors with the E1, E2b, and E3 Genes Deleted," J Virol. 72(2):926-33.

Williams et al. (2009), "Preclinical Models of HPV1 and HPV2 HNSCC in Mice: An Immune Clearance of HPV1 HNSCC," Head Neck. 31(7):911-8.

Gabitzsch et al. (2009), "A preliminary and comparative evaluation of a novel Ad5 [E1-, E2b-] recombinant-based vaccine used to induce cell mediated immune responses," Immunol. Lett. 122(1):44-51.

Gabitzsch et al. (2009), "Novel Adenovirus type 5 vaccine platform induces cellular immunity against HIV-1 Gag, Pol, Nef despite the presence of Ad5 immunity," Vaccine. 27(46):6394-8.

Cassetti, et al., Antitumor efficacy of Venezuelan equine encephalitis virus replicon particles encoding mutated HPV16 E6 and E7 genes, Vaccine, 22(3-4): 520-527, Jan. 2004.

Helt et al., "Inactivation of both the Retinoblastoma Tumor Suppressor and p21 by the Human Papillomavirus Type 16 E7 Oncoprotein is Necessary to Inhibit Cell Cycle Arrest in Human Epithelial Cells" J. of Virology, 76(20): 10559-10568, Jan. 2002.

Jeong et al., "Human papillomavirus type 16 E6 protein interacts with cystic fibrosis transmembrane regulator-associated ligand and promotes E6-associated protein-mediated ubiquitination and proteasomal degradation," Oncogene, 26:487-499, Jul. 2007.

Wieking et al., "A Non-oncogenic HPV 16 E6/E7 Vaccine Enhances Treatment of HPV Expressing Tumors," Cancer Gene Therapy, 19(10): 667-674, Aug. 2012.

\* cited by examiner

POLYNUCLEOTIDES FOR TREATING ONCOGENIC VIRAL POLYPEPTIDE POSITIVE TUMORS

CROSS-REFERENCE TO RELATED APPLICATIONS

This application is a US National Phase filing of PCT/US2013/022696, filed on Jan. 23, 2013, which claims priority to U.S. 61/590,089, filed on Jan. 24, 2012. The disclosure therein is expressly incorporated entirely by reference.

TECHNICAL FIELD

The various embodiments disclosed herein relate to viral vaccines. In particular, the various embodiments relate to viral vaccines for the treatment of cancer.

BACKGROUND

Some viruses, such as papilloma viruses (e.g., HPV16, HPV18), retroviruses (e.g., HTLV, feline leukemia virus), herpes viruses (e.g., Epstein Barr Virus), and hepatitis viruses (e.g., HBV), are known to cause cancer in humans and other animals. While vaccines, which utilize viral coat proteins or virus-like particles, are often successful at preventing infection, there is a need for therapies that treat established disease and virally-associated cancers.

SUMMARY

In some embodiments, an isolated polynucleotide is provided. The isolated polynucleotide can include a first nucleotide sequence encoding a first antigenic polypeptide, where the first antigenic polypeptide comprises an amino acid sequence having at least 70% sequence identity to the amino acid sequence of a first oncogenic viral polypeptide, is capable of initiating an immune response to the first oncogenic viral polypeptide in an immune-competent host, and is non-oncogenic in the immune-competent host. In some embodiments, the polynucleotide includes a second nucleotide sequence encoding a second antigenic polypeptide, where the second antigenic polypeptide comprises an amino acid sequence having at least 70% sequence identity to the amino acid sequence of a second oncogenic viral polypeptide, is capable of initiating an immune response to the second oncogenic viral polypeptide in the immune-competent host, and is non-oncogenic in the immune-competent host.

The virus can be a human papilloma virus. The first oncogenic viral polypeptide can be E6 and the second oncogenic viral polypeptide can be E7.

The first nucleotide sequence can encode SEQ ID NO:2 having a specific mutation, e.g., a point mutation or deletion at L50, a point mutation or deletion at E148, a point mutation or deletion at T149, a point mutation or deletion at Q150, or a point mutation or deletion at L151. The first nucleotide sequence can encode SEQ ID NO:29.

The second nucleotide sequence can encode SEQ ID NO:4 having a specific mutation, e.g., a point mutation or deletion at H2, a point mutation or deletion at C24, a point mutation or deletion at E46, or a point mutation or deletion at L67. The second nucleotide sequence can encode SEQ ID NO:30.

In some embodiments, a composition is provided. The composition comprises a pharmaceutically acceptable carrier and a polynucleotide provided herein. The polynucleotide can include a first nucleotide sequence encoding a first antigenic polypeptide, where the first antigenic polypeptide comprises an amino acid sequence having at least 70% sequence identity to the amino acid sequence of a first oncogenic viral polypeptide, is capable of initiating an immune response to the first oncogenic viral polypeptide in an immune-competent host, and is non-oncogenic in the immune-competent host. In some embodiments, the polynucleotide includes a second nucleotide sequence encoding a second antigenic polypeptide, where the second antigenic polypeptide comprises an amino acid sequence having at least 70% sequence identity to the amino acid sequence of a second oncogenic viral polypeptide, is capable of initiating an immune response to the second oncogenic viral polypeptide in the immune-competent host, and is non-oncogenic in the immune-competent host.

The virus in the provided compositions can be a human papilloma virus. In the provided compositions, the first oncogenic viral polypeptide can be E6 and the second oncogenic viral polypeptide can be E7.

The first nucleotide sequence in the provided compositions can encode SEQ ID NO:2 having a specific mutation, e.g., a point mutation or deletion at L50, a point mutation or deletion at E148, a point mutation or deletion at T149, a point mutation or deletion at Q150, or a point mutation or deletion at L151. The first nucleotide sequence in the provided compositions can encode SEQ ID NO:29.

The second nucleotide sequence in the provided compositions can encode SEQ ID NO:4 having a specific mutation, e.g., a point mutation or deletion at H2, a point mutation or deletion at C24, a point mutation or deletion at E46, or a point mutation or deletion at L67. The second nucleotide sequence in the provided compositions can encode SEQ ID NO:30.

In some embodiments of the provided compositions, the pharmaceutically acceptable carrier in the provided compositions can be an adenovirus envelope.

In some embodiments, a method for killing a cell expressing a first oncogenic viral polypeptide in a subject is provided. The method includes administering to the subject a composition in an amount sufficient to initiate an immune response against the first oncogenic viral peptide, where the composition comprises a pharmaceutically acceptable carrier and a polynucleotide provided herein and the immune response is effective to cause a cytotoxic effect in the cell. The polynucleotide can include a first nucleotide sequence encoding a first antigenic polypeptide, where the first antigenic polypeptide comprises an amino acid sequence having at least 70% sequence identity to the amino acid sequence of a first oncogenic viral polypeptide, is capable of initiating an immune response to the first oncogenic viral polypeptide in an immune-competent host, and is non-oncogenic in the immune-competent host. In some embodiments, the polynucleotide includes a second nucleotide sequence encoding a second antigenic polypeptide, where the second antigenic polypeptide comprises an amino acid sequence having at least 70% sequence identity to the amino acid sequence of a second oncogenic viral polypeptide, is capable of initiating an immune response to the second oncogenic viral polypeptide in the immune-competent host, and is non-oncogenic in the immune-competent host.

In the provided methods, the virus can be a human papilloma virus. In the provided methods, the first oncogenic viral polypeptide can be E6 and the second oncogenic viral polypeptide can be E7.

In the provided methods, the first nucleotide sequence can encode SEQ ID NO:2 having a specific mutation, e.g., a point mutation or deletion at L50, a point mutation or deletion at E148, a point mutation or deletion at T149, a point mutation or deletion at Q150, or a point mutation or deletion at L151. In the provided methods, the first nucleotide sequence can encode SEQ ID NO:29.

In the provided methods, the second nucleotide sequence can encode SEQ ID NO:4 having a specific mutation, e.g., a point mutation or deletion at H2, a point mutation or deletion at C24, a point mutation or deletion at E46, or a point mutation or deletion at L67. In the provided methods, the second nucleotide sequence can encode SEQ ID NO:30.

In some embodiments of the provided methods, the pharmaceutically acceptable carrier can be an adenovirus envelope.

In some embodiments of the provided methods, the cell can be part of a neoplasia. In some embodiments of the provided methods, the cell can be part of a malignant neoplasia.

While multiple embodiments are disclosed, still other embodiments will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

Figure 1:
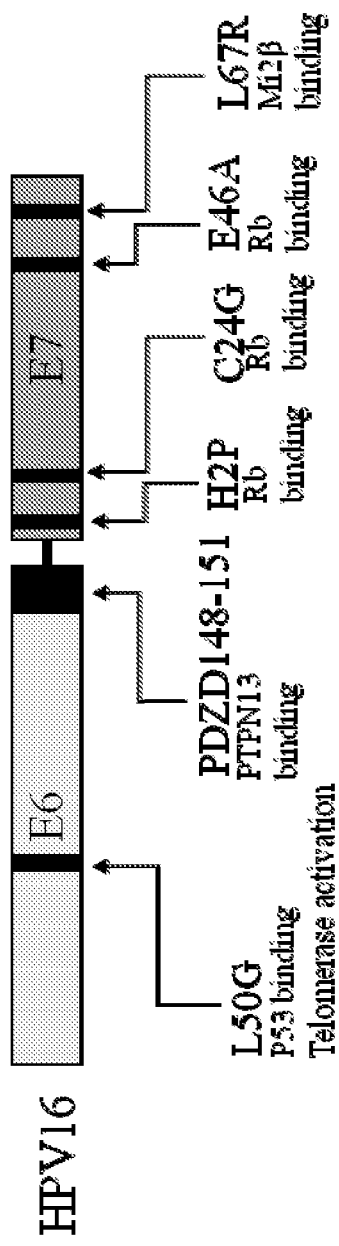
FIG. 1 is a schematic showing mutations in HPV16 E6 and E7.

The various embodiments disclosed herein relate to an antigenic polypeptide that initiates an immune response to an oncogenic viral polypeptide in an immune-competent host, but is non-oncogenic in the immune-competent host. Also provided herein are polynucleotides comprising a sequence encoding such an antigenic polypeptide, compositions comprising such polynucleotides, and methods of use.

As used herein, an oncogenic viral polypeptide is a polypeptide encoded by a viral genome that, when expressed in a host cell, transforms the cell. Oncogenic viral polypeptides include, without limitation, HPV (human papilloma virus)16 E6, HPV16 E7, HPV18 E6, HPV18 E7, HBV (hepatitis B virus) HBXAg, HCV (hepatitis C virus) core protein, HCV NS5A, HTLV (human T-cell lymphotropic virus) TAX, EBV (Epstein-Barr virus) EBNA, and EBV LMP-1. In some embodiments, an oncogenic viral polypeptide (e.g., HPV E6) is sufficient to transform a host cell alone. In other embodiments, an oncogenic viral polypeptide transforms a host cell only in the presence of one or more additional specific cofactors (e.g., other viral oncogenes, host cell gene mutations). For example, HPV E6 can immortalize cells that have a mutation in ErbB2, which can induce invasive growth in some cells.

As used herein, an antigenic polypeptide is a polypeptide that elicits an immune response when present in an immune-competent host. As used herein, an immune-competent host is an animal capable of producing an immune response that results in cytotoxicity (e.g., cytotoxic T-cell-mediated cytotoxicity or antibody-mediated cytotoxicity).

The antigenic polypeptides provided herein are derived from oncogenic viral polypeptides and contain at least one mutation (e.g., a substitution, deletion, or addition of one or more amino acid) as compared to the oncogenic viral polypeptides from which they are derived. An antigenic polypeptide provided herein contains at least one mutation that renders it non-oncogenic under the same conditions under which the oncogenic viral polypeptide from which it is derived transforms a host cell. Mutations that render an oncogenic viral polypeptide non-oncogenic include those that inactivate oncogenic functions, such as, but not limited to, disrupting binding to tumor suppressor proteins, disrupting activation domains, and disrupting binding to DNA. For example, an antigenic polypeptide derived from HPV16 E6 can include a mutation that disrupts a p53 binding site, a telomerase activation site, a PDZ binding domain, or a combination thereof. In another example, an antigenic polypeptide derived from HPV16 E7 can include a mutation that disrupts an Rb protein binding site, an Mi2β binding site, or a combination thereof.

An antigenic polypeptide provided herein has at least 70% sequence identity (e.g., at least 72%, at least 75%, at least 80%, at least 85%, at least 95%, at least 96%, at least 98%, at least 99%, at least 99.5%, or at least 99.7% sequence identity, or from 70% to 99%, from 75% to 99%, from 80% to 99%, or from 88% to 99.9% sequence identity) to an oncogenic viral polypeptide and elicits a cytotoxic immune response to a cell that expresses the oncogenic viral polypeptide. In some embodiments, an antigenic polypeptide and the oncogenic viral polypeptide from which it is derived are about 95.9% identical, about 96.7% identical, about 96.9% identical, about 97.2% identical, about 97.9% identical, about 98.6% identical, about 99% identical, or about 99.3% identical. Examples of antigenic polypeptides include SEQ ID NO:23, SEQ ID NO:24, SEQ ID NO:25, SEQ ID NO:26, SEQ ID NO:27, SEQ ID NO:28, SEQ ID NO:29, SEQ ID NO:30, and SEQ ID NO:31.

"Percent sequence identity" refers to the degree of sequence identity between any given oncogenic viral polypeptide sequence, e.g., SEQ ID NO:2 or SEQ ID NO:4, and an antigenic polypeptide sequence derived therefrom. An antigenic polypeptide typically has a length that is from 70% to 130% percent of the full length of the oncogenic viral polypeptide from which it is derived, e.g., 71%, 74%, 75%, 77%, 80%, 82%, 85%, 87%, 89%, 90%, 93%, 95%, 97%, 99%, 100%, 105%, 110%, 115%, 120%, or 130% of the full length of the oncogenic viral polypeptide from which it is derived. A percent identity for any antigenic polypeptide relative to the oncogenic viral polypeptide from which it is derived can be determined as follows. An oncogenic viral polypeptide (e.g., SEQ ID NO:2 or SEQ ID NO:4) is aligned to one or more candidate sequences using the computer program available under the commercial name ClustalW (version 1.83, default parameters), which allows alignments of nucleic acid or polypeptide sequences to be carried out across their entire length (global alignment). Chema et al., Nucleic Acids Res., 31(13):3497-500 (2003).

ClustalW calculates the best match between a reference (e.g., an oncogenic viral polypeptide) and one or more candidate sequences (e.g., an antigenic polypeptide derived from an oncogenic viral polypeptide), and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple sequence alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the European Bioinformatics Institute site on the World Wide Web (ebi.ac.uk/Tools/msa/clustalw2/), or downloaded from, for example, the Clustal.org site on the World Wide Web (clustal.org/clustal2/).

To determine percent identity of an antigenic polypeptide to an oncogenic viral polypeptide, the sequences are aligned using ClustalW, the number of identical matches in the alignment is divided by the length of the reference sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

Polynucleotides provided herein (e.g., SEQ ID NO:34) include double stranded or single stranded, linear or circular DNA or RNA that comprise a nucleotide sequence encoding an antigenic polypeptide provided herein. In some embodiments, a polynucleotide provided herein includes more than one nucleotide sequence, each encoding an antigenic polypeptide. In some embodiments, a polynucleotide can comprise a concatamer of nucleotide sequences encoding the same antigenic polypeptide.

The polynucleotides provided herein also comprise one or more nucleotide sequences operatively linked to a nucleotide sequence encoding an antigenic polypeptide that promotes expression of protein from the antigenic polypeptide nucleotide sequence(s) contained therein. Such sequences include, without limitation, promoters, enhancers, RNA stabilization sequences, internal ribosomal entry sites (IRES), and protein stabilization sequences. Promoters suitable for use in the provided polynucleotides include, without limitation, SV40 early promoter, CMV immediate early promoter, retroviral long terminal repeats (LTRs), regulatable promoters (e.g., tetracycline or IPTG responsive promoters), and RSV promoter.

When a plurality of nucleotide sequences encoding antigenic polypeptides are included in a polynucleotide provided herein, the polypeptides expressed therefrom can be expressed as separate proteins, e.g., via separate promoters or through the use of an IRES, or they can be expressed as fused proteins.

In some embodiments, a polynucleotide provided herein includes a nucleotide sequence that encodes a protein tag (e.g., myc tag or FLAG tag) operatively linked to antigenic polypeptide nucleotide sequence such that the tag is attached to the antigenic polypeptide when expressed. As used herein, a protein tag is not included in the antigenic polypeptide sequence for the purposes of determining percent sequence identity to the oncogenic viral polypeptide from which it is derived.

In some embodiments, the polynucleotides provided herein include marker sequences that facilitate the detection of the polynucleotides and/or protein expression from the polynucleotides. In some embodiments, a marker sequence can encode a marker protein, such as a fluorescent marker (e.g., GFP, RFP, or YFP) to facilitate detection of protein expression from the polynucleotide. In other embodiments, a marker sequence does not encode a protein, but can be detected using nucleic acid detection techniques, such as polymerase chain reaction. In some embodiments, a marker sequence can be used to disrupt a region in an oncogenic viral polypeptide that contributes to oncogenic activity of the oncogenic viral polypeptide to produce an antigenic polypeptide. In such cases, the marker sequence is not included in the antigenic polypeptide sequence for the purposes of determining percent sequence identity to the oncogenic viral polypeptide from which it is derived, and the remaining sequence can retain 100% sequence identity to the oncogenic viral polypeptide from which it is derived.

A polynucleotide provided herein can be produced using known methods, such as site directed mutagenesis of an oncogenic viral polypeptide-encoding polynucleotide (e.g., SEQ ID NO:1, SEQ ID NO:3, and SEQ ID NO:5).

Any of the polynucleotides provided herein can be incorporated into a pharmaceutically acceptable carrier. Appropriate pharmaceutically acceptable carriers include, without limitation, viral envelopes, cationic lipid carriers, autologous cells, plasmid vectors, and viral vectors. When a polynucleotide provided herein is incorporated into a viral envelope, it may include one or more packaging sequences that support incorporation into the envelope.

In certain implementations, a composition comprising a polynucleotide provided herein and a pharmaceutically acceptable carrier is formulated for introduction (e.g., enterally, transdermally, intravenously, subcutaneously, or intramuscularly) into an immune-competent host. In use, the composition is administered to an immune-competent host at risk of infection by a virus whose genome encodes an oncogenic viral polypeptide. In some embodiments, the composition is administered to an immune-competent host that has already been infected with such a virus, or has cells (e.g., cancer cells) that express an oncogenic viral polypeptide.

When administered to an immune-competent host, according to one embodiment, a composition provided herein elicits a cytotoxic immune response to a cell expressing an oncogenic viral polypeptide. In some embodiments, administration of a composition provided herein can be used to treat, ameliorate, and/or prevent cancer associated with the expression of an oncogenic viral polypeptide in a subject. In some embodiments, administration of a composition provided herein can result in a reduction in a population of cells expressing an oncogenic viral polypeptide. A reduction in a population of cells expressing an oncogenic viral polypeptide can be measured using any appropriate means, such as, for example, measuring a change in size of a tumor comprising cells expressing the oncogenic viral polypeptide, or measuring a change in the number of circulating cancer cells expressing the oncogenic viral polypeptide. In some embodiments, administration of a composition provided herein to a population of subjects with a cancer associated with the expression of an oncogenic viral polypeptide can result in a longer average survival as compared to a control population that has been similarly treated, but without the administration of a composition provided herein.

In some embodiments, the compositions provided herein can be used in combination with one or more standard therapies (e.g., radiation, surgery, or chemotherapy) to treat a subject having a cancer associated with the expression of an oncogenic viral polypeptide. When used in combination with a standard therapy, the compositions provided herein can be administered before, during, or after the administration of the standard therapy. In some embodiments, the timing of administration of a composition provided herein and/or a standard therapy can be adjusted to increase the efficacy of one or both of the composition or the standard therapy. For example, a composition provided herein can be administered as an initial dose followed over time with additional booster doses to increase immune response. In another example, a composition provided herein can be administered before chemotherapy or after immune recovery from chemotherapy to increase the likelihood of a sufficient immune response.

The compositions provided herein can be dosed in an amount sufficient to elicit a cytotoxic immune response. The dose can be adjusted in order to elicit an immune response, yet not induce a systemic adverse reaction to a carrier in the composition. For example, when using an adenoviral carrier, an appropriate dosage can be in the range of about $10^8$ to $10^{12}$ particles per dose. In some embodiments, the dose amount and/or number of doses can be adjusted depending on the type of sequences used to promote expression of the encoded antigenic polypeptide, the strength of the immune response in the subject, or the type of pharmaceutically acceptable carrier used.

The compositions provided herein can be packaged as premixed formulations or as separate components that can be mixed prior to use. In some embodiments, the compositions provided herein can be packaged in individual doses. In other embodiments, the compositions provided herein can be packaged in containers containing multiple dosages that are measured prior to administration. In some embodiments, the compositions provided herein can be formulated as a concentrate that is diluted before administration. In yet other embodiments, the compositions provided herein can be produced by mixing the separate components prior to administration. Packaging can further include appropriate documentation, labeling, and the like.

It is to be understood that the following examples are not intended to limit the scope of the invention.

EXAMPLES

Example 1

Mutagenesis of HPV16 E6/E7 and Viral Construction

HPV16 E6/E7 Mutagenesis.

Six mutations in HPV16 E6 and E7 were introduced into a wild type E6/E7 encoding nucleic acid as shown in FIG. 1 using in vitro site-directed mutagenesis. For the mutation designated L50G, a leucine to glycine mutation was made at position 50 in E6 within a p53 binding and telomerase activation site domain. For the mutation designated PDZ, the C-terminal PDZ binding domain of E6 at residues 146-151 was substituted with four alanine residues. For the mutation designated H2P, a histidine residue was substituted with a proline residue within an Rb binding site in E7 at position 2. For the mutation designated C24G, a cysteine residue was replaced with a glycine residue within an Rb binding site in E7 at position 24. For the mutation designated E46A, a glutamic acid residue was changed to alanine within an Rb binding site in E7 at position 46. For the mutation designated L67R, leucine to arginine mutation was made within an Mi2β binding region of E7 at position 67. Site-directed mutagenesis was performed on a nucleic acid encoding HPV16 E6 and E7 (SEQ ID NO:5) as per manufacturer directions (Agilent Technologies #200521) using the primers listed in Table 1.

TABLE 1

| Mutation | Forward primer | Reverse primer |
| --- | --- | --- |
| L50G | GACTATTTTGCTTTTCGGGATGGATG (SEQ ID NO: 7) | CCCATCTCTATATACTATGCATCCATC (SEQ ID NO: 8) |
| PDZ | GAACTCGTAGAGCAGCCGCGGCGTA (SEQ ID NO: 9) | GTGTATCTCCATGCATGATTACGCCG (SEQ ID NO: 10) |
| H2P | CAGCCGCGGCGTAATCATGCCTGGA (SEQ ID NO: 11) | GCAATGTAGGTGTATCTCCAGGCATG (SEQ ID NO: 12) |
| C24G | CCAGAGACAACTGATCTCTACGGTTA (SEQ ID NO: 13) | GCTGTCATTTAATTGCTCATAACCGTA (SEQ ID NO: 14) |

TABLE 1-continued

| Mutation | Forward primer | Reverse primer |
|---|---|---|
| E46A | GGTCCAGCTGGACAAGCAGCACCGG (SEQ ID NO: 15) | GTAATGGGCTCTGTCCGGTGCTGCTT (SEQ ID NO: 16) |
| L67R | CGTGTGTGCTTTGTACGCACCTCCGA (SEQ ID NO: 17) | GTGTGACTCTACGCTTCGGAGGTGC (SEQ ID NO: 18) |

The mutated construct was cloned into an adenoviral shuttle vector Ad5 VQ. Fidelity of the final construct was verified by direct DNA sequencing.

Viral Construction.

E1 and E2b deficient Ad5 CMV vectors (empty vector designated [E1-, E2b-]) containing mutant E6/E7 (designated [E1-, E2b-]mut-E6/E7) and wildtype E6/E7 (designated [E1-, E2b-]wt-E6/E7) were constructed and produced as previously described (Amalfitano et al. (1998) *J. Virol.* 72(2):926-33). Briefly, the wildtype and mutant E6/E7 sequences were sub-cloned into the E1 region of the Ad5 [E1-, E2b-] vector using a homologous recombination-based approach. The replication deficient virus was propagated in the E.C7 packaging cell line, $CsCl_2$ purified, and titered. Viral infectious titer was determined as plaque forming units (PFU) on an E.C7 cell monolayer. The viral particle (VP) concentration was determined by sodium dodecyl sulfate (SDS) disruption and spectrophotometry at 260 nm and 280 nm. The ratio of VP to plaque forming units (PFU) was 36.7/1 VP/PFU. The mut-E6/E7 insert as well as wt-E6/E7 were then cut and ligated into the retroviral vector pLXSN using EcoRI and BamHI restriction sites. Retrovirus particles were generated in the Phoenix A cell line according to recommended methods (Nolan Lab, Stanford University, California) with polybrene (Sigma H9268) added to a final concentration of 8 μg/ml.

Example 2

Effect of E6/E7 Mutations on Oncogenesis

Oncogenesis in a Human Adenocarcinoma Alveolar Basal Epithelium Cell Line.

Figure 2:
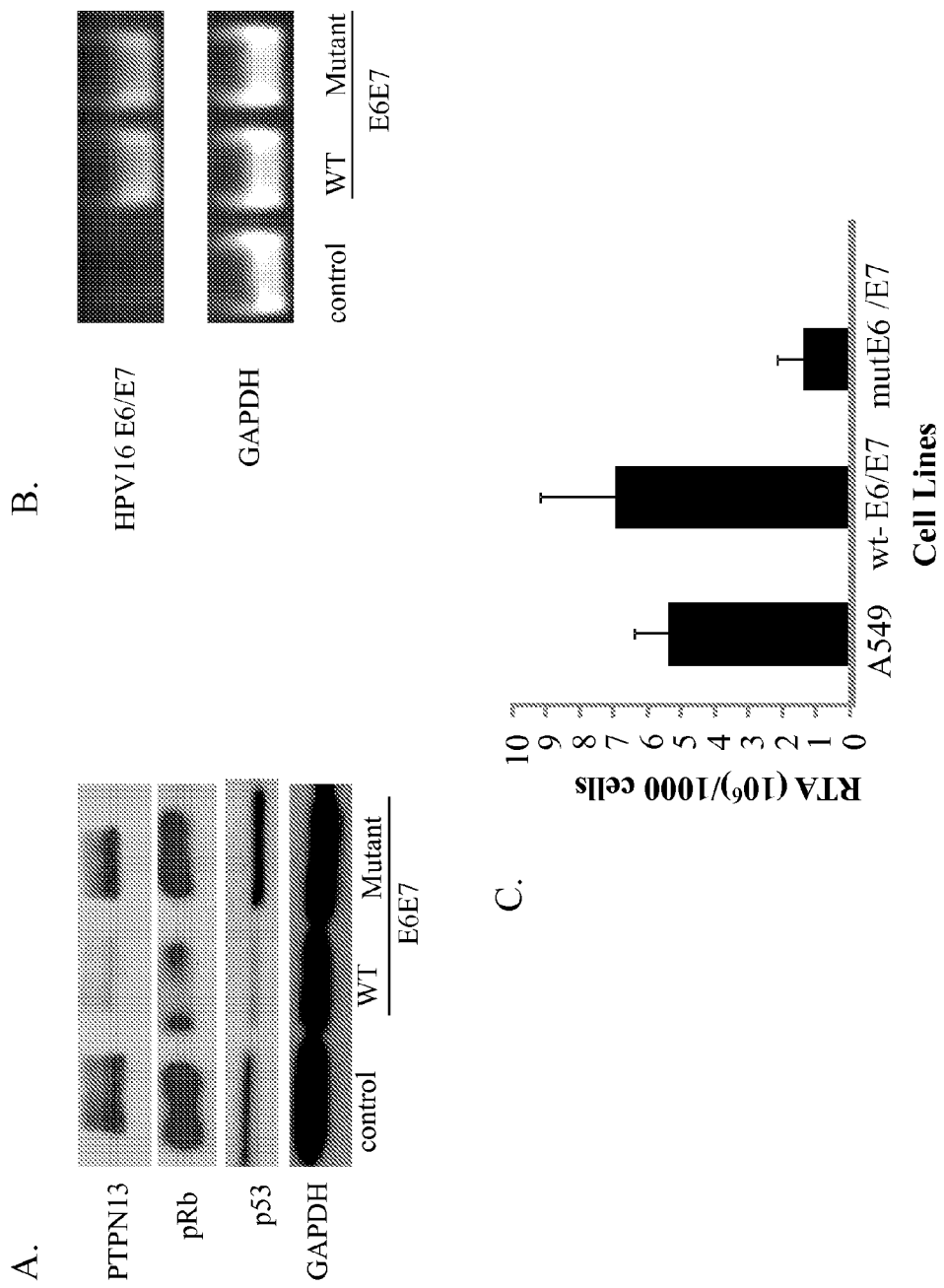
FIG. 2 shows tumor suppressor protein expression (A), HPV16 E6/E7 expression (B), and relative telomerase activity (RTA) (C) in cells infected with a control retrovirus, a retrovirus encoding wild type E6/E7, and a retrovirus encoding a mutant E6/E7.
Figure 3:
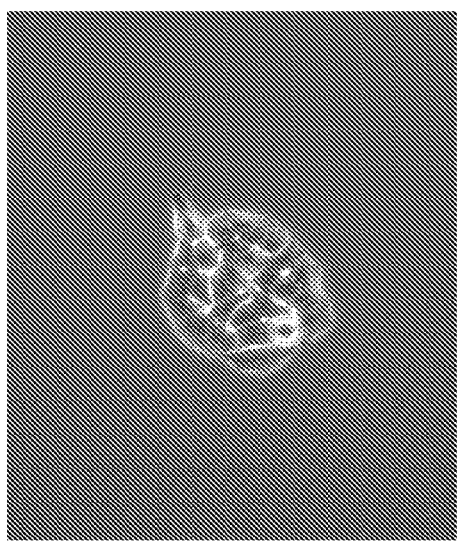
FIG. 3 shows the growth characteristics of cells infected with a control retrovirus (A), a retrovirus encoding wild type E6/E7 (B), and a retrovirus encoding a mutant E6/E7 (C).
Figure 3:
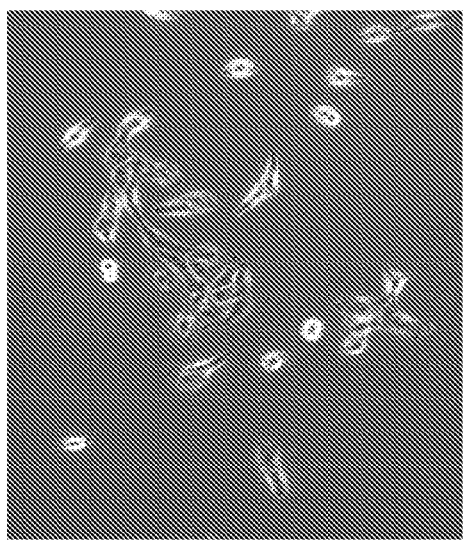
Figure 3:
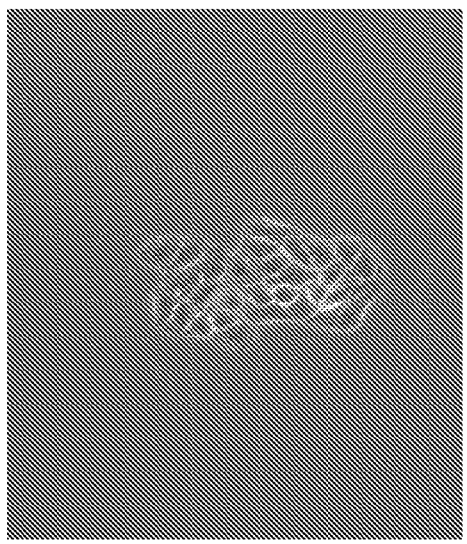

To determine whether the mutated E6/E7 promoted oncogenesis, A549 cells (human adenocarcinoma alveolar basal epithelium cell line) were infected with a retrovirus containing wt-E6/E7 (SEQ ID NO:6), mut-E6/E7 (SEQ ID NO:31), or control vector, and were ring cloned. Clones were analyzed by western blot. FIG. 2A shows that expression of wt-E6/E7 decreases PTPN13, pRb, and p53 protein expression while PTPN13, pRb, and p53 expression levels are similar to control in mut-E6/E7 expressing cells. PCR analysis of clones confirmed that mut-E6/E7 was expressed at levels similar to wt-E6/E7 (FIG. 2B) suggesting that the changes evident by western blot were a consequence of altered E6/E7 function rather than expression levels and confirm an oncogenic loss-of-function in the mut-E6/E7 construct. Telomerase activity was also examined in these clones. The mut-E6/E7 and vector control showed significantly less relative telomerase activity (RTA) compared to the wt-E6/E7 (FIG. 2C). Because wt-E6/E7 induces morphological mesenchymal type changes, the morphological characteristics of clones were also examined. FIG. 3 shows that control and mut-E6/E7 grow in tight colonies, while wt-E6/E7 expression induces a mesenchymal-like change in morphology and cells grow in a non-adherent manner. Together, these data suggest that, unlike expression of wt-E6/E7, stable expression of mut-E6/E7 does not induce the biochemical or morphological changes associated with cellular transformation.

Transformation in Primary Human Epithelial Cells.

Figure 4A:
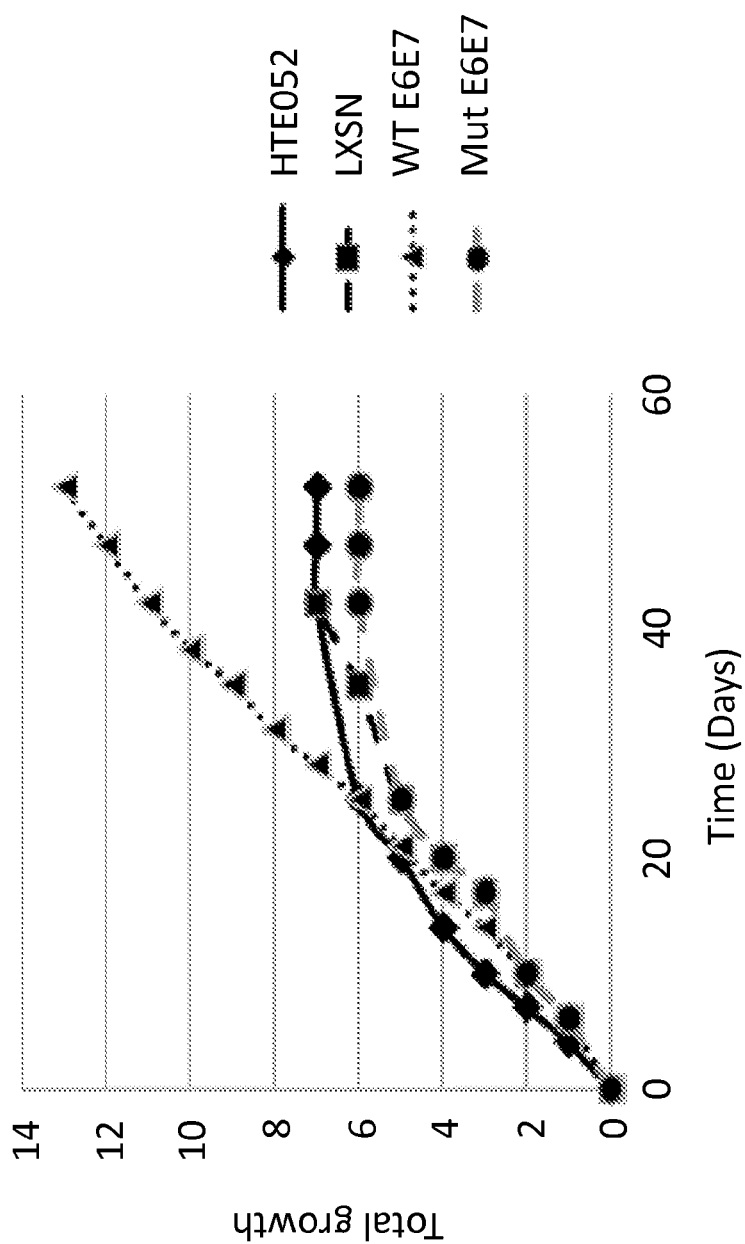
FIG. 4 shows the growth rate (A) and p53 expression of cells infected with a control retrovirus (LXSN), a retrovirus encoding wild type E6/E7, and a retrovirus encoding a mutant E6/E7 (B).

To further show that mut-E6/E7 does not transform cells, primary human tonsil epithelia (HTE) were infected with retrovirus containing wt-E6/E7, mut-E6/E7, or empty vector (LXSN). Uninfected HTE cells (HTE052) served as an additional control. Expression of wt-E6/E7 results in cellular immortalization. However, HTEs expressing mut-E6/E7 and as well as controls, did not immortalize (FIG. 4A). These results demonstrate that stable expression of the mut-E6/E7, even expressed from an integrating retrovirus, does not result in cellular immortalization.

Figure 4B:
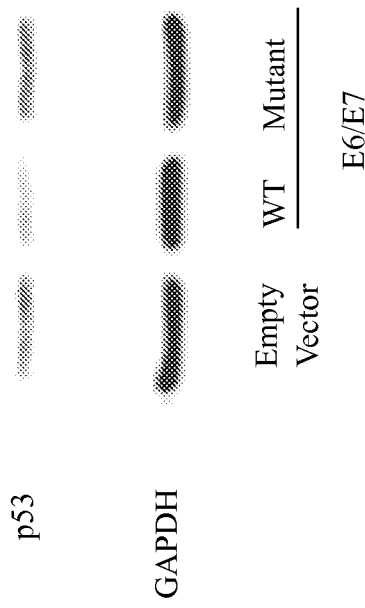
Figure 5:
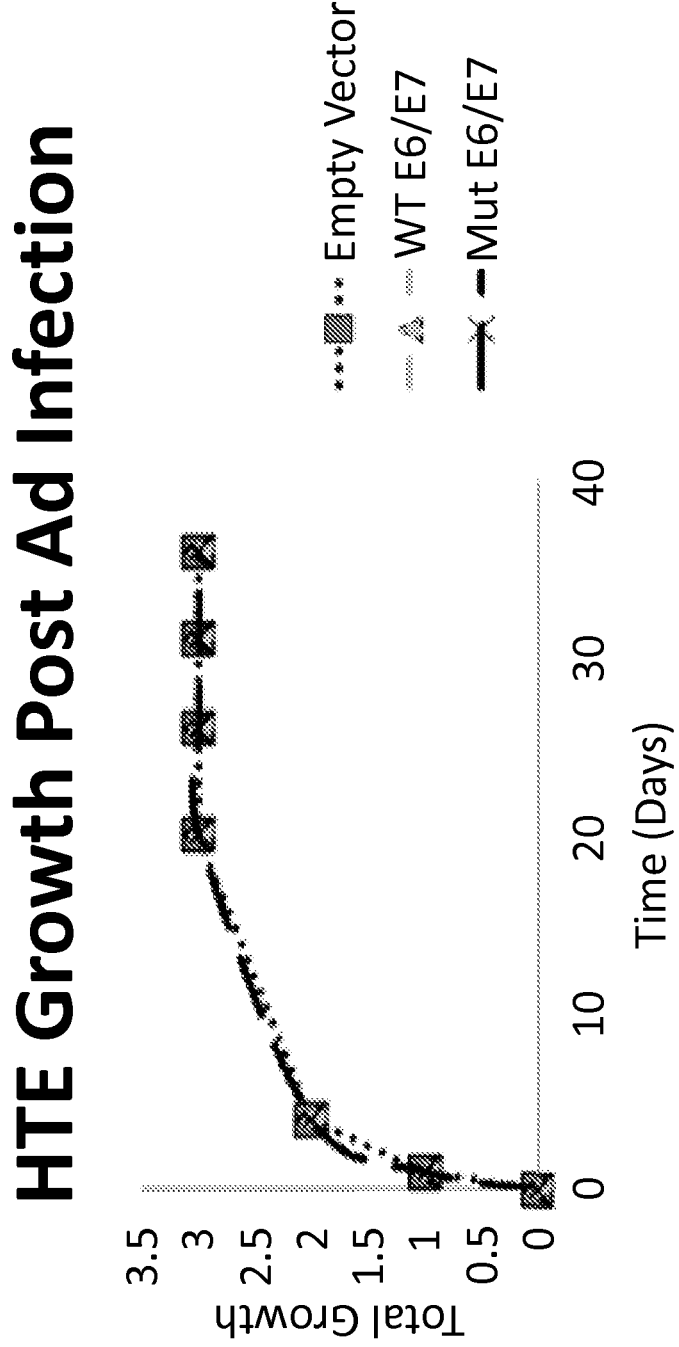
FIG. 5 shows the growth rate of cells infected with an control adenovirus, an adenovirus encoding wild type E6/E7, and an adenovirus encoding a mutant E6/E7.

To determine whether wt-E6/E7 or mut-E6/E7 in a non-replicative adenoviral viral vector infection of primary human tonsillar keratinocytes can result in transformation, HTE were infected with [E1-, E2b-] expressing GFP, [E1-, E2b-]mut-E6/E7, or [E1-, E2b-]wt-E6/E7. Wt-E6/E7 was able to induce loss of p53 (FIG. 4B) however neither wt-E6/E7 or mut-E6/E7 were able to immortalize primary tonsil epithelial cells after infection (FIG. 5). To determine if this was due to viral loss with replication we examine persistence of viral DNA with cell growth. Q-PCR was performed and demonstrated that, as cells replicated, viral DNA was lost at a similar rate with all inserts, suggesting the viral genes did not integrate into the host cell DNA. Therefore HPV genes in the [E1-, E2b-] adenoviral vector does not persist with division and that transient expression of wt-E6/E7 from a replication-deficient adenoviral vector is not sufficient to transform primary cells.

Cell Culture.

A549 cells were grown in Dulbecco's Modified Eagle Medium (Thermo Fisher #SH30022.01) supplemented with 10% Fetal Bovine Serum (Thermo Fisher #SH3007103). Primary human tonsil epithelial cells (HTE) were isolated from surgical tonsillectomy of consented patients under institutional IRB approval using known techniques (Williams et al. (2009) *Head Neck.* 31(7):911-8). Primary HTE were maintained in Keratinocyte SFM media (KSFM, Invitrogen #17005-042).

Retroviral Infection.

HTE and A549 cells were infected with retroviral supernatant containing wt-E6/E7, mut-E6/E7, or empty vector retrovirus and incubated at 37° C. with 5% $CO_2$ overnight. Media was aspirated 24 hours post-infection and fresh media supplemented with neomycin (RPI #G64000) for selection. Individual colonies were ring cloned and put under selection at 800 ug/ml neomycin. Data shown using retrovirally infected clones is representative of multiple clones tested. Due to their density dependence for cell growth, HTE cell lines were not placed under antibiotic selection but maintained in KSFM until cell death or immortalization.

Standard PCR was done to analyze mRNA in stable cell lines expressing LXSN, LXSN wt-E6/E7, or LXSN mut-E6/E7 to validate that the changes made in mut-E6/E7 did not affect E6/E7 transcription rate. PCR was performed using E6/E7 forward primer 5'-CAAACCGTTGTGT-GATTTGTTAATTA-3' (SEQ ID NO:19) and E6/E7 reverse primer 5'-GCTTTTTGTCCAGATGTCTTTGC-3' (SEQ ID NO:20), and expression levels were normalized to GADPH levels using GAPDH forward primer 5'-GGGAAGGT-GAAGGTCGGAGT-3' (SEQ ID NO:21) and GAPDH reverse primer 5'-TGGAAGATGGTGATGGGATTTC-3' (SEQ ID NO:22). All primer concentrations were 450 nM. Preincubation was 94° C. for 10 min. Cycling conditions were 94° C. for 40 sec, 55° C. for 40 sec, and 72° C. for 1 min for a total of 30 cycles.

Adenoviral Infection.

Primary human tonsil epithelial cells grown to 80% confluency were infected with [E1-, E2b-]null, [E1-, E2b-]wt-E6/E7, [E1-, E2b-]mut-E6/E7 or Ad GFP at an MOI of 100 for 24 hours. DNA was collected at passages 4, 5 and 6 post-infection. Cells were trypsinized, rinsed and resuspended in 1× Phosphate Buffered Saline. DNA extraction was performed using standard animal tissue spin-column protocol from DNeasy DNA Blood and Tissue Kit (Qiagen #69504).

Q-PCR.

Quantitative real-time polymerase chain reaction was performed to assay for HPV16 copy number using HPV16 primer set 520 5'-TTGCAGATCATCAAGAACACG-TAGA-3' (SEQ ID NO:32) and 671 5'-CTTGTCCAGCTG-GACCATCTATTT-3' (SEQ ID NO:33). An 18S primer set from Applied Biosystems was used as a control. The amplification reaction included SyberGreen Universal Master Mix (Applied Biosystems), 250 nM (HPV16 primer set) or 100 nM (18S primer set) of each primer, and 25 ng template. Cycling conditions were 95° C. for 10 minutes with 40 cycles at 95° C. for 15 seconds and 60° C. for 60 seconds using the Stratagene Mx3000P thermocycler.

Western Blot Analysis.

Stable cell lines A549 wt-E6/E7, A549 mut-E6/E7 and parental A549 cells were grown to 80-90% confluency, rinsed with PBS and harvested with lysis solution (50 mM Tris HCl pH 7.5; 150 mM NaCl; 5 mM EDTA; 2 mM $Na_3VO_4$; 100 mM NaF; 10 mM NaPPi; 10% glycerol; 1% Triton; 1× Halt Protease Inhibitors; 17.4 μg/μl PMSF). Membranes were pelleted by centrifugation (10,000 rpm at 4° C.) and soluble proteins collected. Total protein was quantified using the BCA protein assay kit as per the manufacturer's directions (Pierce) and equal total protein was analyzed by western blot. Briefly, proteins were separated by SDS-PAGE, transferred to PVDF-membranes (Immobilon-P), blocked with either 5% bovine serum albumin (MP Biomedicals) or non-fat dry milk, and visualized by chemiluminscnence on film or via UVP bioimaging system (Upland, Calif.). Membranes were incubated with the following antibodies: FAP-1 (1:500, Santa Cruz sc15356), p53 (1:500, Calbiochem OP43), pRb (1:250, BD Biosciences 554136) and GAPDH (1:5000, Ambion #Am4300)

Example 3

HPV Specific Cell Mediated Immune Response

Cell Mediated Immunity in Response to Mutant E6/E7.

Figure 6:
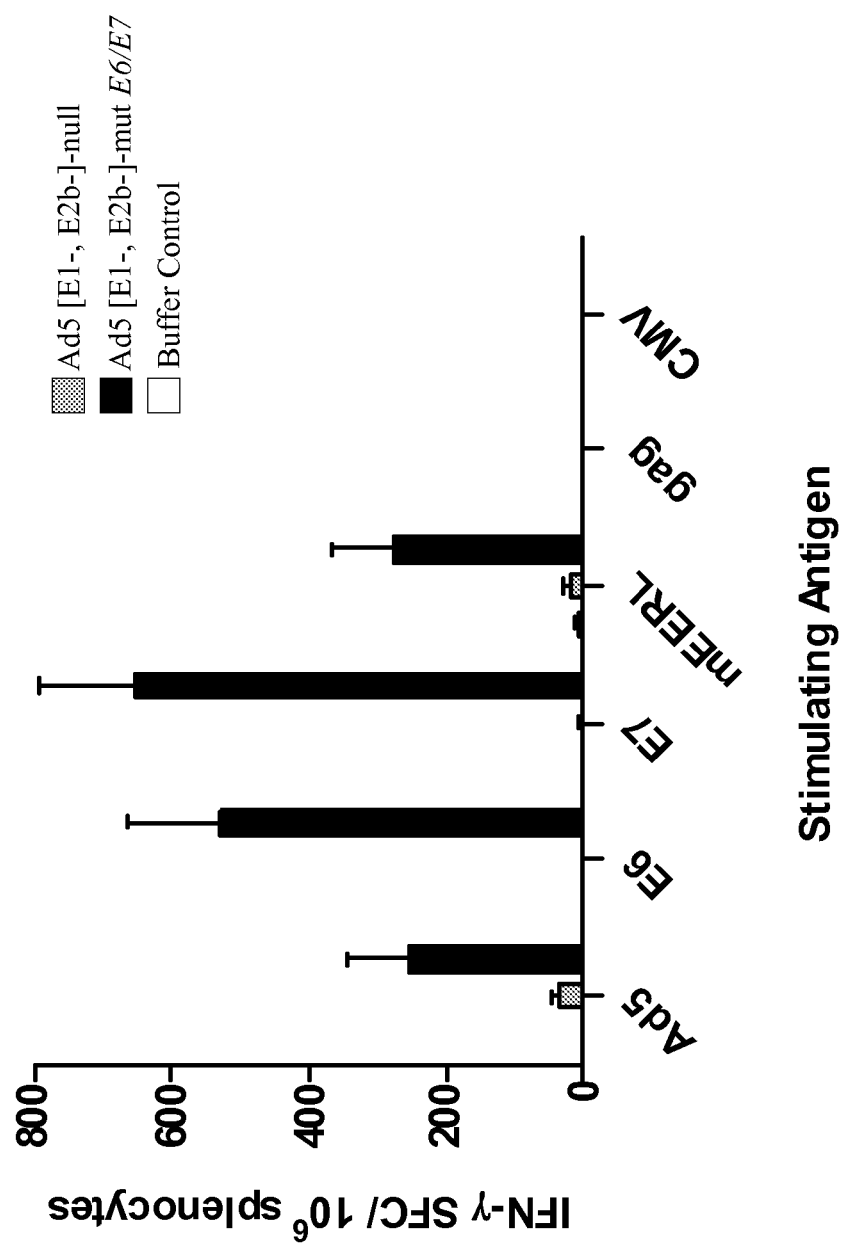
FIG. 6 shows the interferon gamma response of splenocytes from mice immunized with buffer control, control adenovirus (vector control), or adenovirus encoding mutant E6/E7 exposed to the indicated antigen.
Figure 7:
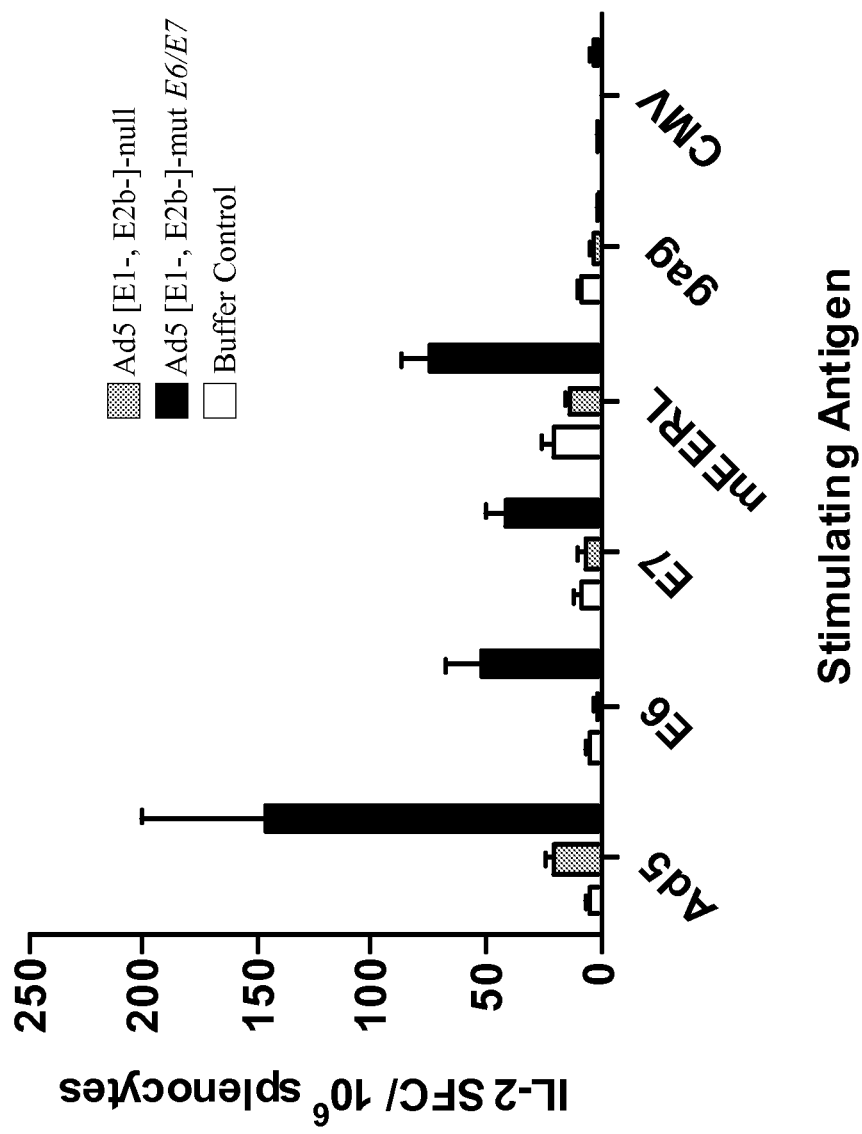
FIG. 7 shows the IL-2 response of splenocytes from mice immunized with buffer control, control adenovirus (vector control), or adenovirus encoding mutant E6/E7 exposed to the indicated antigen.

To determine whether the mutations in E6/E7, rendering them non-oncogenic, alter the ability to mount an HPV-specific immune response in the context of the [E1-, E2b-] adenoviral vector in vitro, spleens were harvested from control and immunized mice and the ability of splenocytes to secrete IFN-γ and IL-2 when stimulated by E6/E7 or lysates from cells immortalized with E6/E7 was examined. Cell mediated immunity (CMI) responses were determined in control non-vaccinated and vaccinated mice by assessing the numbers of IFN-γ and IL-2 secreting cells in splenocytes harvested from groups of individual mice using enzyme-linked immunospot (ELISpot) analysis. As shown in FIGS. 6 and 7, CMI responses were detected in mice immunized with Ad5 [E1-, E2b-]mut-E6/E7. This was demonstrated by significantly elevated levels of IFN-γ (FIG. 6) and IL-2 (FIG. 7) spot forming cells (SFC) induced in immunized mice but not control mice injected with buffer solution or Ad5 [E1-, E2b-]null. Although the IL-2 SFC responses were consistently lower than those observed for IFN-γ, they were significantly elevated above control values. The specificity of the CMI responses was demonstrated by a lack of reactivity when splenocytes from all groups were exposed to irrelevant antigens HIV-gag or CMV. The presence of functionally active splenocytes in all groups of mice was verified by positive responses to concanavalin A (ConA). These results indicate that the non-oncogenic mut-E6/E7 is immunogenic and induces a HPV specific E6/E7 immune response at or above the level of that induced by wt-E6/E7 when expressed from an adenoviral vector.

Animal Immunizations.

All animal studies were performed under approval by the institutional animal care and use review. Male C57Bl/6 mice 8 to 10 weeks old were injected three times subcutaneously at 7 day intervals with a buffer solution (N=4), $10^{10}$ VP Ad5 [E1-, E2b-] null, or $10^{10}$ VP Ad5 [E1-, E2b-] mut-E6/E7. A fourth immunization 2 weeks following the third immunization served as an additional boost injection. Two weeks after the last injection/immunization, all mice were sacrificed and spleens harvested. Splenocytes were isolated for ELISpot testing. Serum from each mouse was collected and stored at −20° C. until testing.

Cell Culture.

Mouse tonsil epithelial cells expressing HPV16 E6, E7, Ras, and luciferace (mEERL) (Williams et al. (2009) *Head. Neck.* 31(7):911-8) were maintained in DMEM supplemented with 22.5% Hams F-12 medium, 10% heat inactivated FCS, 100 U/mL penicillin, 100 μg/mL streptomycin, 0.5 μg/mL hydrocortisone, 0.0084 μg/mL cholera toxin, 5 μg/mL transferrin, 5 μg/mL insulin, 0.00136 μg/mL tri-iodothyronine, and 5 μg/mL EGF.

HPV+ Cell Lysate Preparation.

HPV+ (mEERL) cells were grown in two T125 flask until confluent, after which cells were aseptically scraped off the plastic surface, washed three times with sterile PBS, and re-suspended in 1 mL of sterile PBS. Cells were lysed by freeze-thawing 3 times and cellular debris removed by centrifugation. Soluble protein was brought to a final volume of 2 mL with sterile PBS. The presence of HPV-E7 in the lysate was confirmed by western blot analysis performed as described elsewhere (Gabitzsch et al. (2009) *Immunol. Lett.* 122(1):44-51).

ELISpot Analysis.

HPV16-E6 and E7 specific IFN-γ and IL-2 production from splenocytes isolated from individual mice following immunizations was detected by ELISpot as described elsewhere (Gabitzsch et al. (2009) *Vaccine.* 27(46):6394-8). Briefly, cells were stimulated with HPV16 E6 and E7 peptides (15-mer peptide complete sets for each; JPT Peptide Technologies, Berlin, Germany). Peripheral blood mononuclear cells (PBMC) were used at a concentration of $2\times10^5$ cells/well and reported as the number of spot forming cells (SFC) per $10^6$ cells per well. All E6 peptides were combined and tested as a single pool. Similarly, all E7 peptides were combined and tested as a single pool. Each peptide pool was tested in duplicate. To test for specificity, splenocytes were exposed to an HIV-gag peptide pool and a cytomegalovirus (CMV) peptide pool. Peptides were utilized at 0.1 μg of each peptide/well. To test for reactivity to mEERL cell lysate, 25 μL of lysate was added to test wells in duplicate. In all ELISpot assays, cells stimulated with concanavalin A (ConA) at a concentration of 1 μg/well served as positive controls. Colored SFC were counted using an Immunospot ELISpot plate reader (Cellular Technology, Shaker Heights, Ohio) and responses considered positive if, 1) 50 SFC were detected/$10^6$ cells after subtraction of the negative control or 2) SFC were at least 2-fold greater than those in the negative control wells and significantly elevated.

Statistical Analysis.

Statistically significant differences in the mean immune responses between groups of animals were determined by Student's t-test with a P-value of 0.05 or lower being considered significant, using GraphPad Prism (GraphPad Software, Inc.).

Example 4

Survival in an HPV+ Tumor Model

Figure 8:
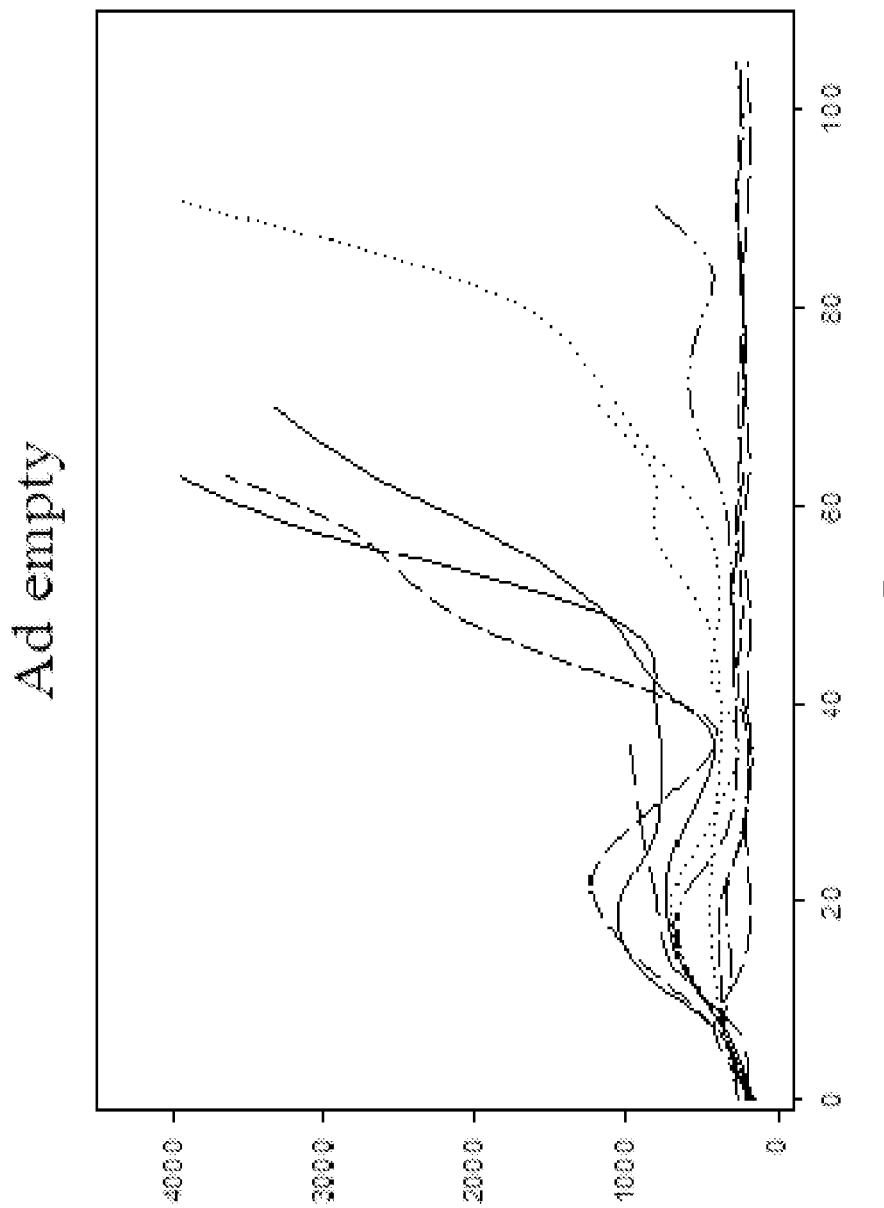
FIG. 8 shows HPV+ tumor growth in mice vaccinated with control adenovirus (vector control), adenovirus encoding mutant E6/E7, or adenovirus encoding wild type E6/E7. Each line indicates tumor growth in an individual mouse.
Figure 8:
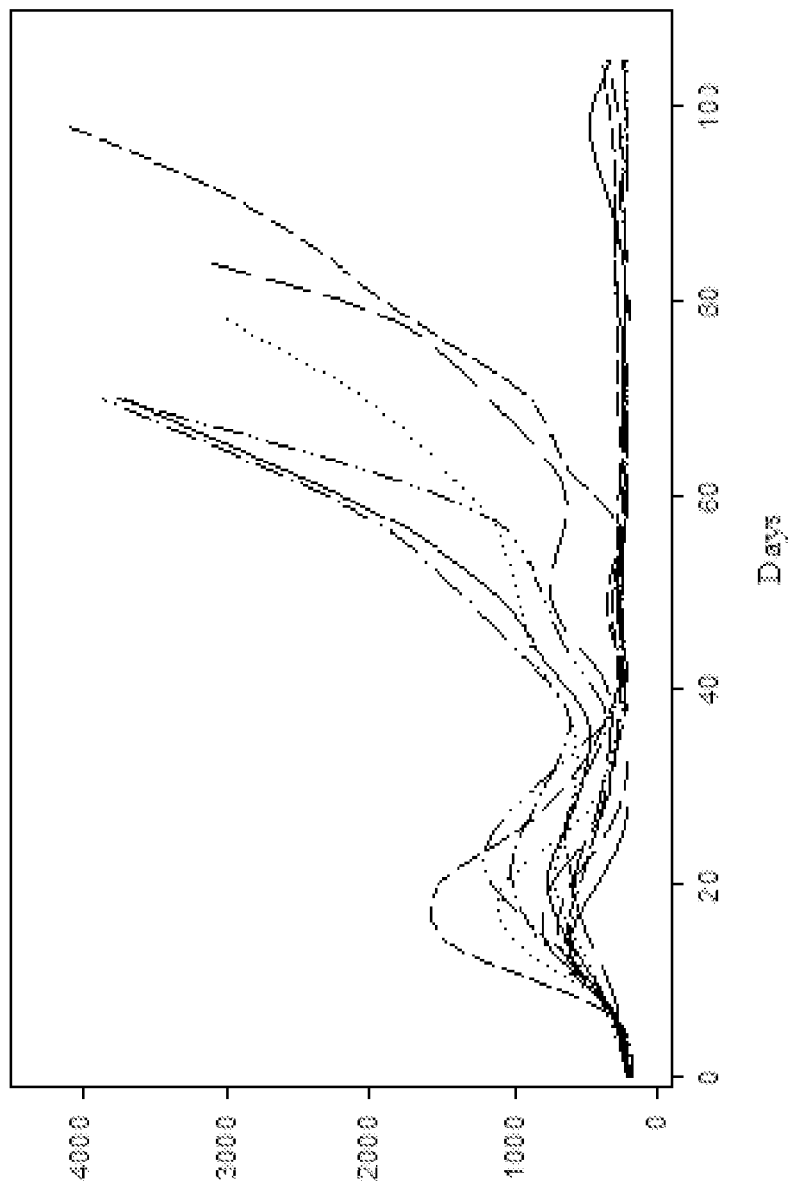
Figure 8:
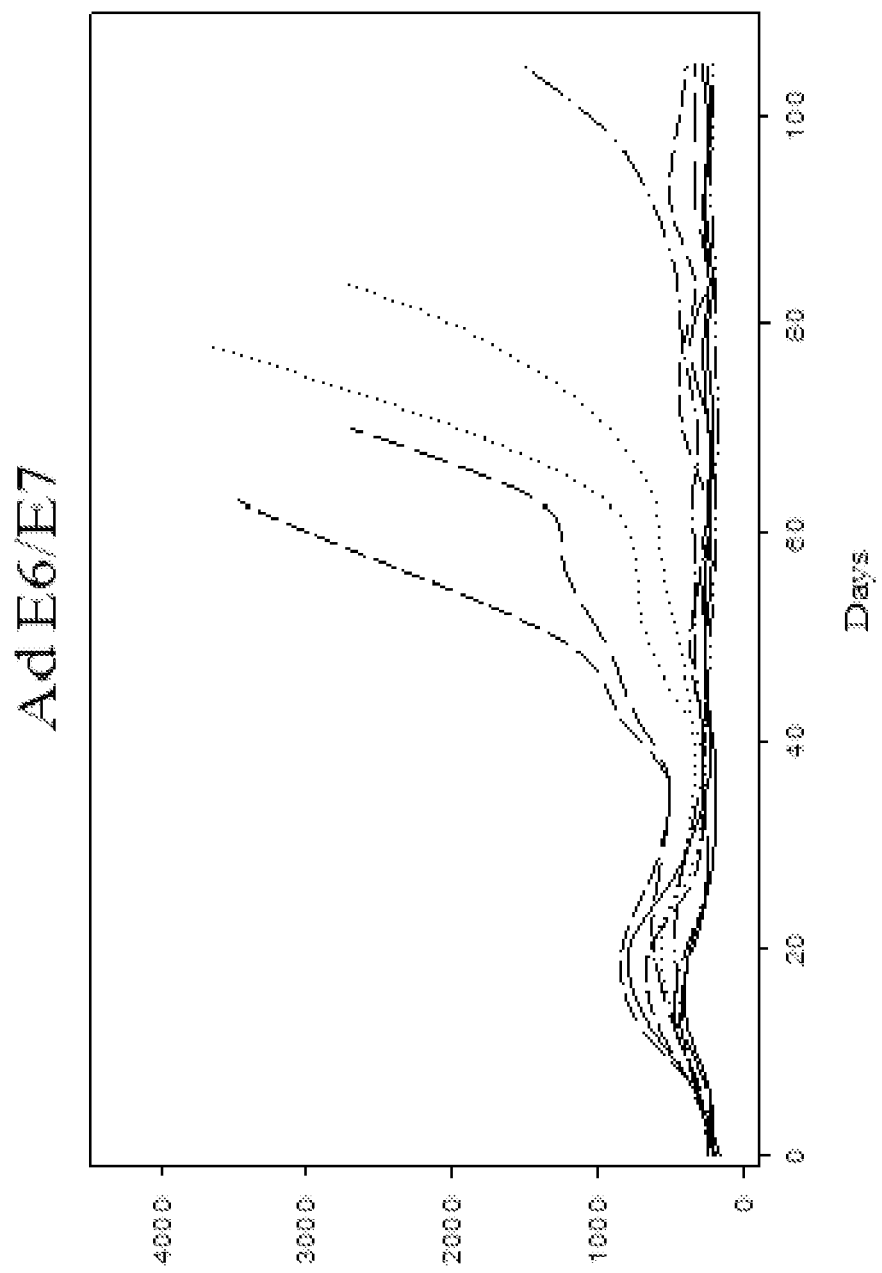
Figure 9:
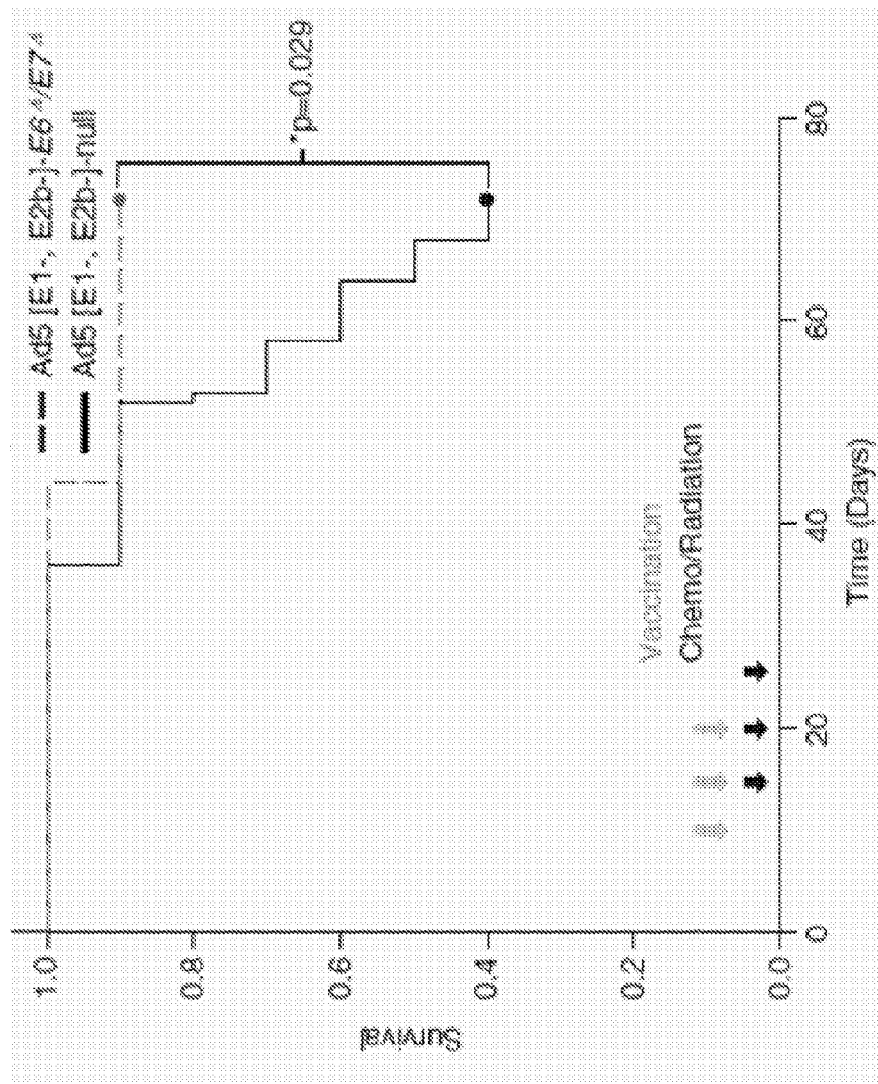
FIG. 9 shows survival in mice implanted with HPV+ cancer cells and vaccinated with control adenovirus (Ad5 [E1-,E2b-]-null), or adenovirus encoding mutant E6/E7 (Ad5 [E1-, E2b-]-E6$^\Delta$/E7$^\Delta$).

To test whether an immune response to non-oncogenic mut-E6/E7 would synergize with chemoradiation as wt-E6/E7 has been demonstrated to do in an adenovirus background, a mouse model of HPV+ related HNSCC was used. HPV+ tumors were generated in wildtype mice which then received intranasal immunization with adenovirus expressing mut-E6/E7 (Ad5 [E1-, E2b-]-E6$^\Delta$/E7$^\Delta$) or adenovirus control (Ad5 [E1-,E2b-]-null) in conjunction with cisplatin and radiation (cisplatin/xrt). Mice receiving only cisplatin/xrt (historical data) or cisplatin/xrt+[E1-, E2b-] vector control (Ad empty) had similar tumor growth and long term survival. However, mice receiving mut-E6/E7 or wt-E6/E7 had significantly improved survival. The mut-E6/E7 mice showed the best overall control of tumor growth and survival (FIGS. 8 and 9). These data confirm that mut-E6/E7 enhances immune related clearance in vivo during standard therapy for HPV related cancer.

Cell Culture.

mEERL were maintained as described in Example 3.

HPV+ Cell Preparation.

HPV+ (mEERL) cells were grown in a single T125 flask until confluent, after which cells were scraped off the plastic surface and washed.

Tumor Models.

Male C57BlJ/6 mice were obtained from the Jackson Labs and maintained by Sanford Research LARF in accordance with USDA guidelines. All experiments were approved by Sanford Research IACUC and performed within institutional guidelines. Briefly, using a 23-gauge needle 1×$10^6$ mEERL cells were implanted subcutaneously in the right hind flank of mice. After palpable tumors were present, on days 7, 14, and 21, mice were given $10^{10}$ viral particles adenovirus control (Ad5 [E1-,E2b-]-null), or adenovirus encoding mut-E6/E7 (Ad5 [E1-, E2b-]-E6$^\Delta$/E7$^\Delta$) intranasally. Cisplatin was dissolved in bacteriostatic 0.9% sodium chloride (Hospira Inc. Lake Forest, Ill.) at 20 mg/$m^2$ and administered intraperitoneally at 13, 20, and 27 days post tumor implantation. Mice were treated with 8Gy X-ray radiation therapy (RadSource RS2000 irradiator, Brentwood, Tenn.) concurrently with cisplatin treatment. Growth of tumors was monitored weekly using caliper measurements and tumor volume calculated using the following formula, volume=(width$^2$)(depth). Mice were euthanized when tumors reached 1.5 cm in any dimension, the animal became emaciated, or demonstrated functional leg impairment. Long-term survival was followed for greater than 70 days.

Example 5

Other Oncogenic Viral Polypeptides

The approach outlined in Examples 1-4 can be used to produce polypeptides derived from other oncogenic viral polypeptides that are effective for initiating an immune response to the respective oncogenic viral polypeptide.

In an example, one or both of EBV oncogenes LMP and EBNA are altered to make them non-oncogenic. Such altered EBV oncogenes are used as a therapy, either alone or in combination with cisplatin and/or radiation, for nasopharyngeal cancer.

In another example, an HPV oncogene is altered in order to treat Kaposi's Sarcoma.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

What is claimed is:

1. An isolated polynucleotide comprising at least one nucleotide sequence encoding at least two antigenic polypeptides, wherein said at least two antigenic polypeptides:
   (a) comprise (i) a first antigenic polypeptide comprising an amino acid sequence having at least 85% sequence identity over its length to the amino acid sequence of SEQ ID NO:2 and having a point mutation compared to SEQ ID NO:2 at each of L50, E148, T149, Q150, and L151; and
      (ii) a second antigenic polypeptide comprising an amino acid sequence having at least 85% sequence identity over its length to the amino acid sequence of SEQ ID NO:4 and having a point mutation compared to SEQ ID NO:4 at each of H2, C24, E46, and L67;
   (b) are capable of initiating an immune response to the oncogenic viral polypeptide in an immune-competent host; and
   (c) are non-oncogenic in the immune-competent host.

2. The polynucleotide of claim 1, wherein (i) the first antigenic polypeptide comprises an amino acid sequence having at least 95% sequence identity over its length to the amino acid sequence of SEQ ID NO:2; and (ii) the second antigenic polypeptide comprises an amino acid sequence having at least 95% sequence identity over its length to the amino acid sequence of SEQ ID NO:4.

3. The polynucleotide of claim 1, wherein (i) the first antigenic polypeptide has L50G, E148A, T149A, Q150A, and L151A point mutations compared to SEQ ID NO:2; and (ii) the second antigenic polypeptide has H2P, C24G, E46A, and L67R point mutations compared to SEQ ID NO:4.

4. The polynucleotide of claim 1, wherein the at least one nucleotide sequence comprises sequences that encode SEQ ID NO:29 and SEQ ID NO:30.

5. A composition comprising:
   (a) a pharmaceutically acceptable carrier; and
   (b) the polynucleotide of claim 1.

6. The composition of claim 5, wherein (i) the first antigenic polypeptide comprises an amino acid sequence having at least 95% sequence identity over its length to the amino acid sequence of SEQ ID NO:2, and (ii) the second antigenic polypeptide comprises an amino acid sequence having at least 95% sequence identity over its length to the amino acid sequence of SEQ ID NO:4.

7. The composition of claim 5, wherein (i) the first antigenic polypeptide has L50G, E148A, T149A, Q150A, and L151A point mutations compared to SEQ ID NO:2, and (ii) the second antigenic polypeptide has H2P, C24G, E46A, and L67R point mutations compared to SEQ ID NO:4.

8. The composition of claim 5, wherein the at least one nucleotide sequence comprises sequences that encode SEQ ID NO:29 and SEQ ID NO:30.

9. The composition of claim 5, wherein the pharmaceutically acceptable carrier is an adenovirus envelope.

10. A method for killing a cell expressing at least one oncogenic viral polypeptide in a subject, the method comprising administering to the subject the composition of claim 5 in an amount sufficient to initiate an immune response against said at least one oncogenic viral peptide.

11. The method of claim 10, wherein said cell is part of a neoplasia.

12. The method of claim 11, wherein said neoplasia is malignant.

13. The method of claim 10, wherein the at least one nucleotide sequence comprise sequences that encode SEQ ID NO:29 and SEQ ID NO:30.

14. The method of claim 10, wherein the pharmaceutically acceptable carrier is an adenovirus envelope.

15. An isolated polynucleotide comprising a nucleotide sequence that encodes sequences selected from the group consisting of SEQ ID NO: 29 and SEQ ID NO: 30.

* * * * *

SEQUENCE LISTING

```
<160> NUMBER OF SEQ ID NOS: 34

<210> SEQ ID NO 1
<211> LENGTH: 456
<212> TYPE: DNA
<213> ORGANISM: Human papillomavirus type 16

<400> SEQUENCE: 1
atgtttcagg acccacagga gcgacccaga aagttaccac agttatgcac agagctgcaa       60
acaactatac atgatataat attagaatgt gtgtactgca agcaacagtt actgcgacgt      120
gaggtatatg actttgcttt tcgggattta tgcatagtat atagagatgg gaatccatat      180
gctgtatgtg ataaatgttt aaagttttat tctaaaatta gtgagtatag acattattgt      240
tatagtttgt atggaacaac attagaacag caatacaaca aaccgttgtg tgatttgtta      300
```

```
attaggtgta ttaactgtca aaagccactg tgtcctgaag aaaagcaaag acatctggac    360
aaaaagcaaa gattccataa tataaggggt cggtggaccg gtcgatgtat gtcttgttgc    420
agatcatcaa gaacacgtag agaaacccag ctgtaa                             456
```

<210> SEQ ID NO 2
<211> LENGTH: 151
<212> TYPE: PRT
<213> ORGANISM: Human papillomavirus type 16

<400> SEQUENCE: 2

```
Met Phe Gln Asp Pro Gln Glu Arg Pro Arg Lys Leu Pro Gln Leu Cys
1               5                  10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg His Tyr Cys
65                  70                  75                  80

Tyr Ser Leu Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150
```

<210> SEQ ID NO 3
<211> LENGTH: 297
<212> TYPE: DNA
<213> ORGANISM: Human papillomavirus type 16

<400> SEQUENCE: 3

```
atgcatggag atacacctac attgcatgaa tatatgttag atttgcaacc agagacaact     60
gatctctact gttatgagca attaaatgac agctcagagg aggaggatga aatagatggt    120
ccagctggac aagcagaacc ggacagagcc cattacaata ttgtaacctt ttgttgcaag    180
tgtgactcta cgcttcggtt gtgcgtacaa agcacacacg tagacattcg tactttggaa    240
gacctgttaa tgggcacact aggaattgtg tgccccatct gttctcagaa accataa      297
```

<210> SEQ ID NO 4
<211> LENGTH: 98
<212> TYPE: PRT
<213> ORGANISM: Human papillomavirus type 16

<400> SEQUENCE: 4

```
Met His Gly Asp Thr Pro Thr Leu His Glu Tyr Met Leu Asp Leu Gln
1               5                  10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45
```

Arg Ala His Tyr Asn Ile Val Thr Phe Cys Cys Lys Cys Asp Ser Thr
            50                  55                  60

Leu Arg Leu Cys Val Gln Ser Thr His Val Asp Ile Arg Thr Leu Glu
 65                  70                  75                  80

Asp Leu Leu Met Gly Thr Leu Gly Ile Val Cys Pro Ile Cys Ser Gln
                85                  90                  95

Lys Pro

<210> SEQ ID NO 5
<211> LENGTH: 753
<212> TYPE: DNA
<213> ORGANISM: Human papillomavirus type 16

<400> SEQUENCE: 5
atgtttcagg acccacagga gcgacccaga aagttaccac agttatgcac agagctgcaa     60
acaactatac atgatataat attagaatgt gtgtactgca agcaacagtt actgcgacgt    120
gaggtatatg actttgcttt tcgggattta tgcatagtat atagagatgg gaatccatat    180
gctgtatgtg ataaatgttt aaagttttat tctaaaatta gtgagtatag acattattgt    240
tatagtttgt atggaacaac attagaacag caatacaaca accgttgtg tgatttgtta    300 attaggtgta ttaactgtca aaagccactg tgtcctgaag aaaagcaaag acatctggac    360
aaaaagcaaa gattccataa tataagggt cggtggaccg tcgatgtat gtcttgttgc    420 agatcatcaa gaacacgtag agaaacccag ctgtaaatgc atggagatac acctacattg    480
catgaatata tgttagattt gcaaccagag acaactgatc tctactgtta tgagcaatta    540
aatgacagct cagaggagga ggatgaaata gatggtccag ctggacaagc agaaccggac    600
agagcccatt acaatattgt aacctttttgt tgcaagtgtg actctacgct tcggttgtgc    660
gtacaaagca cacacgtaga cattcgtact ttggaagacc tgttaatggg cacactagga    720
attgtgtgcc ccatctgttc tcagaaacca taa                                  753

<210> SEQ ID NO 6
<211> LENGTH: 249
<212> TYPE: PRT
<213> ORGANISM: Human papillomavirus type 16

<400> SEQUENCE: 6

Met Phe Gln Asp Pro Gln Glu Arg Pro Arg Lys Leu Pro Gln Leu Cys
  1               5                  10                  15

Thr Glu Leu Gln Thr Thr Ile His Asp Ile Ile Leu Glu Cys Val Tyr
                20                  25                  30

Cys Lys Gln Gln Leu Leu Arg Arg Glu Val Tyr Asp Phe Ala Phe Arg
            35                  40                  45

Asp Leu Cys Ile Val Tyr Arg Asp Gly Asn Pro Tyr Ala Val Cys Asp
        50                  55                  60

Lys Cys Leu Lys Phe Tyr Ser Lys Ile Ser Glu Tyr Arg His Tyr Cys
 65                  70                  75                  80

Tyr Ser Leu Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg

```
                 130                 135                 140
Thr Arg Arg Glu Thr Gln Leu Met His Gly Asp Thr Pro Thr Leu His
145                 150                 155                 160

Glu Tyr Met Leu Asp Leu Gln Pro Glu Thr Thr Asp Leu Tyr Cys Tyr
                165                 170                 175

Glu Gln Leu Asn Asp Ser Ser Glu Glu Asp Glu Ile Asp Gly Pro
            180                 185                 190

Ala Gly Gln Ala Glu Pro Asp Arg Ala His Tyr Asn Ile Val Thr Phe
            195                 200                 205

Cys Cys Lys Cys Asp Ser Thr Leu Arg Leu Cys Val Gln Ser Thr His
        210                 215                 220

Val Asp Ile Arg Thr Leu Glu Asp Leu Leu Met Gly Thr Leu Gly Ile
225                 230                 235                 240

Val Cys Pro Ile Cys Ser Gln Lys Pro
                245

<210> SEQ ID NO 7
<211> LENGTH: 26
<212> TYPE: DNA
<213> ORGANISM: Artificial Sequence
<220> FEATURE:
<223> OTHER INFORMATION: primer

<400> SEQUENCE: 7
gactattttg cttttcggga tggatg                                  26

<210> SEQ ID NO 8
<211> LENGTH: 27
<212> TYPE: DNA
<213> ORGANISM: Artificial Sequence
<220> FEATURE:
<223> OTHER INFORMATION: primer

<400> SEQUENCE: 8
cccatctcta tactatgc atccatc                                   27

<210> SEQ ID NO 9
<211> LENGTH: 25
<212> TYPE: DNA
<213> ORGANISM: Artificial Sequence
<220> FEATURE:
<223> OTHER INFORMATION: primer

<400> SEQUENCE: 9
gaactcgtag agcagccgcg gcgta                                   25

<210> SEQ ID NO 10
<211> LENGTH: 26
<212> TYPE: DNA
<213> ORGANISM: Artificial Sequence
<220> FEATURE:
<223> OTHER INFORMATION: primer

<400> SEQUENCE: 10
gtgtatctcc atgcatgatt acgccg                                  26

<210> SEQ ID NO 11
<211> LENGTH: 25
<212> TYPE: DNA
<213> ORGANISM: Artificial Sequence
<220> FEATURE:
<223> OTHER INFORMATION: primer
```

<400> SEQUENCE: 11
cagccgcggc gtaatcatgc ctgga                                    25

<210> SEQ ID NO 12
<211> LENGTH: 26
<212> TYPE: DNA
<213> ORGANISM: Artificial Sequence
<220> FEATURE:
<223> OTHER INFORMATION: primer

<400> SEQUENCE: 12
gcaatgtagg tgtatctcca ggcatg                                   26

<210> SEQ ID NO 13
<211> LENGTH: 26
<212> TYPE: DNA
<213> ORGANISM: Artificial Sequence
<220> FEATURE:
<223> OTHER INFORMATION: primer

<400> SEQUENCE: 13
ccagagacaa ctgatctcta cggtta                                   26

<210> SEQ ID NO 14
<211> LENGTH: 27
<212> TYPE: DNA
<213> ORGANISM: Artificial Sequence
<220> FEATURE:
<223> OTHER INFORMATION: primer

<400> SEQUENCE: 14
gctgtcattt aattgctcat aaccgta                                  27

<210> SEQ ID NO 15
<211> LENGTH: 25
<212> TYPE: DNA
<213> ORGANISM: Artificial Sequence
<220> FEATURE:
<223> OTHER INFORMATION: primer

<400> SEQUENCE: 15
ggtccagctg gacaagcagc accgg                                    25

<210> SEQ ID NO 16
<211> LENGTH: 26
<212> TYPE: DNA
<213> ORGANISM: Artificial Sequence
<220> FEATURE:
<223> OTHER INFORMATION: primer

<400> SEQUENCE: 16
gtaatgggct ctgtccggtg ctgctt                                   26

<210> SEQ ID NO 17
<211> LENGTH: 26
<212> TYPE: DNA
<213> ORGANISM: Artificial Sequence
<220> FEATURE:
<223> OTHER INFORMATION: primer

<400> SEQUENCE: 17
cgtgtgtgct ttgtacgcac ctccga                                   26

<210> SEQ ID NO 18
<211> LENGTH: 25

```
<212> TYPE: DNA
<213> ORGANISM: Artificial Sequence
<220> FEATURE:
<223> OTHER INFORMATION: primer

<400> SEQUENCE: 18
gtgtgactct acgcttcgga ggtgc                                           25

<210> SEQ ID NO 19
<211> LENGTH: 26
<212> TYPE: DNA
<213> ORGANISM: Artificial Sequence
<220> FEATURE:
<223> OTHER INFORMATION: primer

<400> SEQUENCE: 19
caaaccgttg tgtgatttgt taatta                                          26

<210> SEQ ID NO 20
<211> LENGTH: 23
<212> TYPE: DNA
<213> ORGANISM: Artificial Sequence
<220> FEATURE:
<223> OTHER INFORMATION: primer

<400> SEQUENCE: 20 gcttttgtc cagatgtctt tgc                                              23

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
gggaaggtga aggtcggagt                                                 20

<210> SEQ ID NO 22
<211> LENGTH: 22
<212> TYPE: DNA
<213> ORGANISM: Artificial Sequence
<220> FEATURE:
<223> OTHER INFORMATION: primer

<400> SEQUENCE: 22
tggaagatgg tgatgggatt tc                                              22

<210> SEQ ID NO 23
<211> LENGTH: 151
<212> TYPE: PRT
<213> ORGANISM: Artificial Sequence
<220> FEATURE:
<223> OTHER INFORMATION: Human papillomavirus type 16 E6 L50G mutant

<400> SEQUENCE: 23
```

Met Phe Gln Asp Pro Gln Glu Arg Pro Arg Lys Leu Pro Gln Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Gly Cys Ile Val Tyr Arg Asp Gly Asn Pro Tyr Ala Val Cys Asp
    50                  55                  60

```
Lys Cys Leu Lys Phe Tyr Ser Lys Ile Ser Glu Tyr Arg His Tyr Cys
 65                  70                  75                  80

Tyr Ser Leu Tyr Gly Thr Thr Leu Glu Gln Gln Tyr Asn Lys Pro Leu
                 85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150
```

<210> SEQ ID NO 24
<211> LENGTH: 151
<212> TYPE: PRT
<213> ORGANISM: Artificial Sequence
<220> FEATURE:
<223> OTHER INFORMATION: Human papillomavirus type 16 E6 PDZ mutant

<400> SEQUENCE: 24

```
Met Phe Gln Asp Pro Gln Glu Arg Pro Arg Lys Leu Pro Gln Leu Cys
1               5                   10                  15

Thr Glu Leu Gln Thr Thr Ile His Asp Ile Ile Leu Glu Cys Val Tyr
                 20                  25                  30

Cys Lys Gln Gln Leu Leu Arg Arg Glu Val Tyr Asp Phe Ala Phe Arg
             35                  40                  45

Asp Leu Cys Ile Val Tyr Arg Asp Gly Asn Pro Tyr Ala Val Cys Asp
 50                  55                  60

Lys Cys Leu Lys Phe Tyr Ser Lys Ile Ser Glu Tyr Arg His Tyr Cys
 65                  70                  75                  80

Tyr Ser Leu Tyr Gly Thr Thr Leu Glu Gln Gln Tyr Asn Lys Pro Leu
                 85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Ala Ala Ala Ala
145                 150
```

<210> SEQ ID NO 25
<211> LENGTH: 98
<212> TYPE: PRT
<213> ORGANISM: Artificial Sequence
<220> FEATURE:
<223> OTHER INFORMATION: Human papillomavirus type 16 E7 H2P mutant

<400> SEQUENCE: 25

```
Met Pro Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
                 20                  25                  30

Glu Glu Glu Asp Glu Ile Asp Gly Pro Ala Gly Gln Ala Glu Pro Asp
             35                  40                  45

Arg Ala His Tyr Asn Ile Val Thr Phe Cys Cys Lys Cys Asp Ser Thr
 50                  55                  60
```

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 26
<211> LENGTH: 98
<212> TYPE: PRT
<213> ORGANISM: Artificial Sequence
<220> FEATURE:
<223> OTHER INFORMATION: Human papillomavirus type 16 E7 C24G mutant

<400> SEQUENCE: 26

Met His Gly Asp Thr Pro Thr Leu His Glu Tyr Met Leu Asp Leu Gln
1               5                   10                  15

Pro Glu Thr Thr Asp Leu Tyr Gly Tyr Glu Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 27
<211> LENGTH: 98
<212> TYPE: PRT
<213> ORGANISM: Artificial Sequence
<220> FEATURE:
<223> OTHER INFORMATION: Human papillomavirus type 16 E7 E46A mutant

<400> SEQUENCE: 27

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Ala Ala Pro Asp
            35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 28
<211> LENGTH: 98
<212> TYPE: PRT
<213> ORGANISM: Artificial Sequence
<220> FEATURE:
<223> OTHER INFORMATION: Human papillomavirus type 16 E7 L67R mutant

<400> SEQUENCE: 28

```
Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
    50                  55                  60

Leu Arg Arg Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 29
<211> LENGTH: 151
<212> TYPE: PRT
<213> ORGANISM: Artificial Sequence
<220> FEATURE:
<223> OTHER INFORMATION: Human papillomavirus type 16 E6 L50G/PDZ mutant

<400> SEQUENCE: 29

Met Phe Gln Asp Pro Gln Glu Arg Pro Arg Lys Leu Pro Gln Leu Cys
1               5                   10                  15

Thr Glu Leu Gln Thr Thr Ile His Asp Ile Ile Leu Glu Cys Val Tyr
                20                  25                  30

Cys Lys Gln Gln Leu Leu Arg Arg Glu Val Tyr Asp Phe Ala Phe Arg
            35                  40                  45

Asp Gly Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg His Tyr Cys
65                  70                  75                  80

Tyr Ser Leu Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Ala Ala Ala Ala
145                 150

<210> SEQ ID NO 30
<211> LENGTH: 98
<212> TYPE: PRT
<213> ORGANISM: Artificial Sequence
<220> FEATURE:
<223> OTHER INFORMATION: Human papillomavirus type 16 E7
      H2P/C24G/E46A/L67R mutant

<400> SEQUENCE: 30

Met Pro Gly Asp Thr Pro Thr Leu His Glu Tyr Met Leu Asp Leu Gln
1               5                   10                  15

Pro Glu Thr Thr Asp Leu Tyr Gly Tyr Glu Gln Leu Asn Asp Ser Ser
                20                  25                  30

Glu Glu Glu Asp Glu Ile Asp Gly Pro Ala Gly Gln Ala Ala Pro Asp
            35                  40                  45
```

```
Arg Ala His Tyr Asn Ile Val Thr Phe Cys Cys Lys Cys Asp Ser Thr
            50                  55                  60

Leu Arg Arg Cys Val Gln Ser Thr His Val Asp Ile Arg Thr Leu Glu
 65                  70                  75                  80

Asp Leu Leu Met Gly Thr Leu Gly Ile Val Cys Pro Ile Cys Ser Gln
                 85                  90                  95

Lys Pro

<210> SEQ ID NO 31
<211> LENGTH: 249
<212> TYPE: PRT
<213> ORGANISM: Artificial Sequence
<220> FEATURE:
<223> OTHER INFORMATION: HPV type 16 E6 L50G/PDZ E7 H2P/C24G/E46A/L67R
      mutant

<400> SEQUENCE: 31

Met Phe Gln Asp Pro Gln Glu Arg Pro Arg Lys Leu Pro Gln Leu Cys
 1               5                  10                  15

Thr Glu Leu Gln Thr Thr Ile His Asp Ile Ile Leu Glu Cys Val Tyr
                20                  25                  30

Cys Lys Gln Gln Leu Leu Arg Arg Glu Val Tyr Asp Phe Ala Phe Arg
             35                  40                  45

Asp Gly Cys Ile Val Tyr Arg Asp Gly Asn Pro Tyr Ala Val Cys Asp
 50                  55                  60

Lys Cys Leu Lys Phe Tyr Ser Lys Ile Ser Glu Tyr Arg His Tyr Cys
 65                  70                  75                  80

Tyr Ser Leu Tyr Gly Thr Thr Leu Glu Gln Gln Tyr Asn Lys Pro Leu
                 85                  90                  95

Cys Asp Leu Leu Ile Arg Cys Ile Asn Cys Gln Lys Pro Leu Cys Pro
                100                 105                 110

Glu Glu Lys Gln Arg His Leu Asp Lys Lys Gln Arg Phe His Asn Ile
            115                 120                 125

Arg Gly Arg Trp Thr Gly Arg Cys Met Ser Cys Cys Arg Ser Ser Arg
130                 135                 140

Thr Arg Arg Ala Ala Ala Ala Met Pro Gly Asp Thr Pro Thr Leu His
145                 150                 155                 160

Glu Tyr Met Leu Asp Leu Gln Pro Glu Thr Thr Asp Leu Tyr Gly Tyr
                165                 170                 175

Glu Gln Leu Asn Asp Ser Ser Glu Glu Glu Asp Glu Ile Asp Gly Pro
            180                 185                 190

Ala Gly Gln Ala Ala Pro Asp Arg Ala His Tyr Asn Ile Val Thr Phe
        195                 200                 205

Cys Cys Lys Cys Asp Ser Thr Leu Arg Arg Cys Val Gln Ser Thr His
    210                 215                 220

Val Asp Ile Arg Thr Leu Glu Asp Leu Leu Met Gly Thr Leu Gly Ile
225                 230                 235                 240

Val Cys Pro Ile Cys Ser Gln Lys Pro
                245

<210> SEQ ID NO 32
<211> LENGTH: 25
<212> TYPE: DNA
<213> ORGANISM: Artificial Sequence
<220> FEATURE:
<223> OTHER INFORMATION: primer
```

```
<400> SEQUENCE: 32
ttgcagatca tcaagaacac gtaga                                              25

<210> SEQ ID NO 33
<211> LENGTH: 23
<212> TYPE: DNA
<213> ORGANISM: Artificial Sequence
<220> FEATURE:
<223> OTHER INFORMATION: primer

<400> SEQUENCE: 33
cttgtccagc tggaccatct att                                                23

<210> SEQ ID NO 34
<211> LENGTH: 755
<212> TYPE: DNA
<213> ORGANISM: Artificial Sequence
<220> FEATURE:
<223> OTHER INFORMATION: HPV type 16 E6 L50G/PDZ E7 H2P/C24G/E46A/L67R
      mutant

<400> SEQUENCE: 34
atgtttcagg acccacagga gcgacccaga aagttaccac agttatgcac agagctgcaa        60
acaactatac atgatataat attagaatgt gtgtactgca agcaacagtt actgcgacgt       120
gaggtatatg actttgcttt tcgggatgga tgcatagtat atagagatgg gaatccatat       180
gctgtatgtg ataaatgttt aaagttttat tctaaaatta gtgagtatag acattattgt       240
tatagtttgt atggaacaac attagaacag caatacaaca aaccgttgtg tgatttgtta       300
attaggtgta ttaactgtca aaagccactg tgtcctgaag aaaagcaaag acatctggac       360
aaaaagcaaa gattccataa tataagggggt cggtggaccg gtcgatgtat gtcttgttgc      420
agatcatcaa gaactcgtag agcagccgcg gcgtaatcat gcctggagat acacctacat       480
tgcatgaata tatgttagat ttgcaaccag agacaactga tctctacggt tatgagcaat       540
taaatgacag ctcagaggag gaggatgaaa tagatggtcc agctggacaa gcagcaccgg       600
acagagccca ttacaatatt gtaaccttt gttgcaagtg tgactctacg cttcggaggt        660
gcgtacaaag cacacacgta gacattcgta ctttggaaga cctgttaatg ggcacactag       720
gaattgtgtg ccccatctgt tctcagaaac cataa                                  755
```